(12) United States Patent
Chen et al.

(10) Patent No.: US 10,344,258 B2
(45) Date of Patent: Jul. 9, 2019

(54) SORTING DEVICE AND SORTING METHOD

(71) Applicant: NATIONAL TSING HUA UNIVERSITY, Hsinchu (TW)

(72) Inventors: Chih-Chen Chen, Hsinchu (TW); Yi-Hsing Hsiao, Hsinchu (TW)

(73) Assignee: NATIONAL TSING HUA UNIVERSITY, Hsinchu (TW)

(*) Notice: Subject to any disclaimer, the term of this patent is extended or adjusted under 35 U.S.C. 154(b) by 413 days.

(21) Appl. No.: 15/081,149

(22) Filed: Mar. 25, 2016

(65) Prior Publication Data

US 2017/0121665 A1    May 4, 2017

(30) Foreign Application Priority Data

Nov. 3, 2015  (TW) .............................. 104136127 A (51) Int. Cl.
| | | |
|---|---|---|
| *G01N 33/561* | (2006.01) | |
| *C12M 1/00* | (2006.01) | |
| *G01N 27/447* | (2006.01) | |
| *B01D 57/02* | (2006.01) | |
| *B01L 3/00* | (2006.01) | |
| *C12N 7/00* | (2006.01) | |
| *C12N 13/00* | (2006.01) | |

(52) U.S. Cl.
CPC ............ *C12M 47/04* (2013.01); *B01D 57/02* (2013.01); *B01L 3/5027* (2013.01); *B01L 3/502715* (2013.01); *C12M 45/07* (2013.01); *C12N 7/00* (2013.01); *C12N 13/00* (2013.01); *G01N 27/44739* (2013.01); *G01N 27/44747* (2013.01); *G01N 27/44773* (2013.01); *G01N 33/561* (2013.01); *B01L 2200/0652* (2013.01); *B01L 2300/0816* (2013.01); *B01L 2300/0867* (2013.01); *B01L 2400/0415* (2013.01); *B01L 2400/0421* (2013.01)

(58) Field of Classification Search
None
See application file for complete search history.

(56) References Cited

U.S. PATENT DOCUMENTS

| | | | |
|---|---|---|---|
| 6,361,958 B1 * | 3/2002 | Shieh | .................. B01L 3/5027 366/DIG. 2 |
| 6,740,492 B2 | 5/2004 | Merril | |
| 7,638,464 B2 | 12/2009 | Fagnani et al. | |

(Continued)

FOREIGN PATENT DOCUMENTS

| | | |
|---|---|---|
| TW | I314212 B | 9/2009 |
| TW | I415941 B | 11/2013 |

*Primary Examiner* — Erik B Crawford
(74) *Attorney, Agent, or Firm* — Muncy, Geissler, Olds & Lowe, P.C.

(57) ABSTRACT

A sorting device is provided. The sorting device includes: a carrier substrate; an input unit disposed on the carrier substrate for inputting a biological sample into the sorting device; a porous material disposed on the carrier substrate and adjacent to the input unit, wherein the porous material contains antigen molecules having specificity to a target biological analyte; a driving module generating at least one driving force in the porous material so as to sort the biological sample based on the affinity for the antigen and the driving force; and an output unit disposed on the carrier substrate and adjacent to the porous material for collecting the sorted target biological analyte. A sorting method is also provided.

13 Claims, 7 Drawing Sheets

(56) References Cited

U.S. PATENT DOCUMENTS

| | | | |
|---|---|---|---|
| 2003/0087290 A1* | 5/2003 | Tarlov | B01L 3/5023 |
| | | | 435/6.11 |
| 2008/0161193 A1 | 7/2008 | Stroobant | |
| 2009/0318303 A1* | 12/2009 | Delamarche | B01L 3/502707 |
| | | | 506/9 |
| 2010/0285136 A1 | 11/2010 | Eiden et al. | |
| 2011/0177618 A1* | 7/2011 | Herr | B01L 3/502761 |
| | | | 436/515 |
| 2015/0293089 A1* | 10/2015 | Araz | B01L 3/5027 |
| | | | 506/9 |

\* cited by examiner

SORTING DEVICE AND SORTING METHOD

CROSS REFERENCE TO RELATED APPLICATION

This application claims the benefits of the Taiwan Patent Application Serial Number 104136127, filed on Nov. 3, 2015, the subject matter of which is incorporated herein by reference.

BACKGROUND OF THE INVENTION

1. Field of the Invention

The present invention relates to a sorting device and a sorting method, more particularly, to a sorting device and a sorting method for sorting a target biological analyte.

2. Description of Related Art

The research of the interaction between biomolecules and their characteristics (such as antibodies, antigens, proteins, enzymes, metabolites, nucleic acids, drugs, and deoxyribonucleic acids (DNA)) becomes a major topic in various fields (such as drug development, genetic engineering, biochemistry, biotechnology, and molecular biology, etc.).

Take bacteriophage as an example, phage display is a technique that has been widely used. The main advantage of phage display is to provide a substantially physical connection for the phenotype and the genotype of the bacteriophage, and may be produced in large quantities. For example, the DNA sequence of the protein analyte may be spliced to the DNA sequence of the coat protein of the bacteriophage, therefore, when the protein analyte is successfully expressed on the surface of the bacteriophage through the coat protein of the bacteriophage, the protein analyte can be sorted together with the bacteriophage.

Currently, the most commonly used method for sorting bacteriophages is the biopanning process, which generally consists of the following steps: 1) fixing antigen molecules onto a solid surface, a column, or a biosensor chip (such as a Biacore sensor chip), wherein the antigen may seize positive strains of bacteriophages that have high affinity for the antigen; 2) removing unbound or negative strains of bacteriophages after extensive washing; 3) eluting bound bacteriophages subsequently using an elution buffer; and 4) amplifying the eluted bacteriophages using bacteria for hosts and conducting further rounds of affinity enrichment if needed. Usually, three to five repeated rounds of capture, wash, and amplification steps must be carried out in order to attain desired sorting efficiency. However, the total amount of time required to complete the process of biopanning can be longer than a month.

Accordingly, sorting bacteriophage is time-consuming and costly due to the process of biopanning and the subsequent analysis and evaluation processes, such as enzyme-linked immunosorbent assay (ELISA) and DNA sequencing.

Therefore, it is desirable to provide a simple, fast and efficient sorting platform for sorting a target biological analyte from a biological sample.

SUMMARY OF THE INVENTION

An embodiment of the present invention provides a sorting device, comprising: a carrier substrate; an input unit disposed on the carrier substrate for inputting a biological sample into the sorting device; a porous material disposed on the carrier substrate and adjacent to the input unit, wherein the porous material contains an antigen having specificity to a target biological analyte; a driving module generating at least one driving force in the porous material so as to sort the biological sample based on the affinity for the antigen and the driving force; and an output unit disposed on the carrier substrate and adjacent to the porous material for collecting the sorted biological analyte.

The driving force is a stream force, an electric field force, or a combination thereof. The driving force comprises a first driving force and a second driving force in different directions, wherein a direction of the second driving force is toward the output unit. An intensity of the first driving force differs from an intensity of the second driving force, and the intensity of the second driving force is greater than the intensity of the first driving force.

Preferably, the driving module comprises an electric field generating unit disposed on an external region of the carrier substrate for generating a first electric field and a second electric field in the porous material, wherein a direction of the first electric field and a direction of the second electric field are different from each other and are substantially perpendicular to each other. The first electric field provides the first driving force and the second electric field provides the second driving force.

Another embodiment of the present invention provides a sorting method, comprising the steps of: providing a porous material, wherein the porous material comprises a specific antigen for a target biological analyte; introducing a biological sample including the target biological analyte to the porous material; generating at least one driving force in the porous material; and sorting the target biological analyte from the biological sample through an affinity between the target biological analyte and the antigen, and through the driving force.

In the step of generating at least one driving force in the porous material, the driving force is a stream force, an electric field force, or a combination thereof. Preferably, the driving force is performed by an electric field generating unit for generating a first electric field and a second electric field in the porous material, wherein a direction of the first electric field is substantially perpendicular to a direction of the second electric field, and an intensity of the first electric field differs from an intensity of the second electric field. The intensity of the first electric field is weaker than the intensity of the second electric field, and a biological analyte other than the target biological analyte unbound to the antigen is expelled out from the porous material along the direction of the first electric field.

Preferably, the first electric field and the second electric field are alternatively generated in the porous material by the electric field generating unit, and the alternating frequency of the first electric field and the second electric field is 0.1 to 5 times per minute or 0.5 to 1.5 times per minute. A difference between the intensity of the first electric field and the intensity of the second electric field is 0.1 V/cm to 20 V/cm, or 0.5 V/cm to 10 V/cm.

Further, the target biological analyte may be selected from the group consisting of bacteriophages, antibodies, antigens, proteins, enzymes, metabolites, nucleic acids, drugs, and deoxyribonucleic acids (DNA), but is not limited thereby. However, the target biological analyte is preferably bacteriophage in the present invention.

BRIEF DESCRIPTION OF THE DRAWINGS

Hereafter, examples will be provided to illustrate the embodiments of the present invention. It should be noted that these accompanying figures are illustrative and are not drawn to scale. The scale of each component may be arbitrarily enlarged or downsized in order to clearly show the technical feature of the present invention. Also, in the present specification and figures, the same or similar components will be shown by similar symbols.

DETAILED DESCRIPTION OF THE PREFERRED EMBODIMENT

Hereafter, embodiments or examples will be provided for implementing different technical features of the present invention. The examples of the specific components and their arrangement will be described for illustrating the features of the present invention. However, these examples are illustrative, and the scope of the present invention should not be limited thereby. For example, when a first element is formed on a second element, the practical condition may include the case that the first element is formed directly on the second element, and the case that another element is formed between the first element and the second element. Further, it should be noted that labels and symbols in different embodiments may be used repeatedly; these repeated labels and symbols are used for clear description of the present disclosure and do not represent any particular relations between different embodiments and/or structures.

In addition, the spatially related terms such as "under", "below", "over", "above", "between", and other similar terms are used for describing relationship between one (or more) element or feature and another (or more) element or feature. The spatial relationships described by these spatially related terms may include different orientations when the device is in use or in operation and the directions described in figures. These spatially related terms indicate the same spatial relationships within elements even if the device is rotated in different directions (rotated in 90 degrees or other directions). It should be realized that additional steps may be performed before, in between, or after any steps of the disclosed method, and some of the steps may be replaced or deleted in different embodiments.

Furthermore, the term "perpendicular" refers to an angle substantially being 90 degrees, and may be an angle of 90±10 degrees. In some embodiments, it may refer to an angle of 90±5 degrees.

The present invention provides a sorting device and a sorting method using the same. The sorting device and the sorting method for sorting bacteriophage will be described as an example in the following description. However, the present invention is applicable for sorting other biological analytes such as antibodies, antigens, proteins, enzymes, metabolites, nucleic acids, drugs, and deoxyribonucleic acids (DNA), but the analyte is not limited thereby as long as an analyte may have an affinity for a corresponding antigen.

In the present embodiment, an antigen having specificity to a target biological analyte (bacteriophage) is fixed to a porous material, and two electric fields with different intensity and being perpendicular to each other are generated in the porous material for sorting the positive strains of bacteriophages with strong affinity for the antigen. The sorted positive strains of bacteriophages may further be separated into a plurality of channels of the microfluidic channel unit according to affinity strength between the antigen and the sorted positive strains of bacteriophages.

Further, the target bacteriophage may be sorted continuously using the sorting device of the present invention, and the duration time for a single sorting cycle is short. The sorted bacteriophage may be applied directly without other tests (such as ELISA) for detection or evaluation.

Figure 1A:
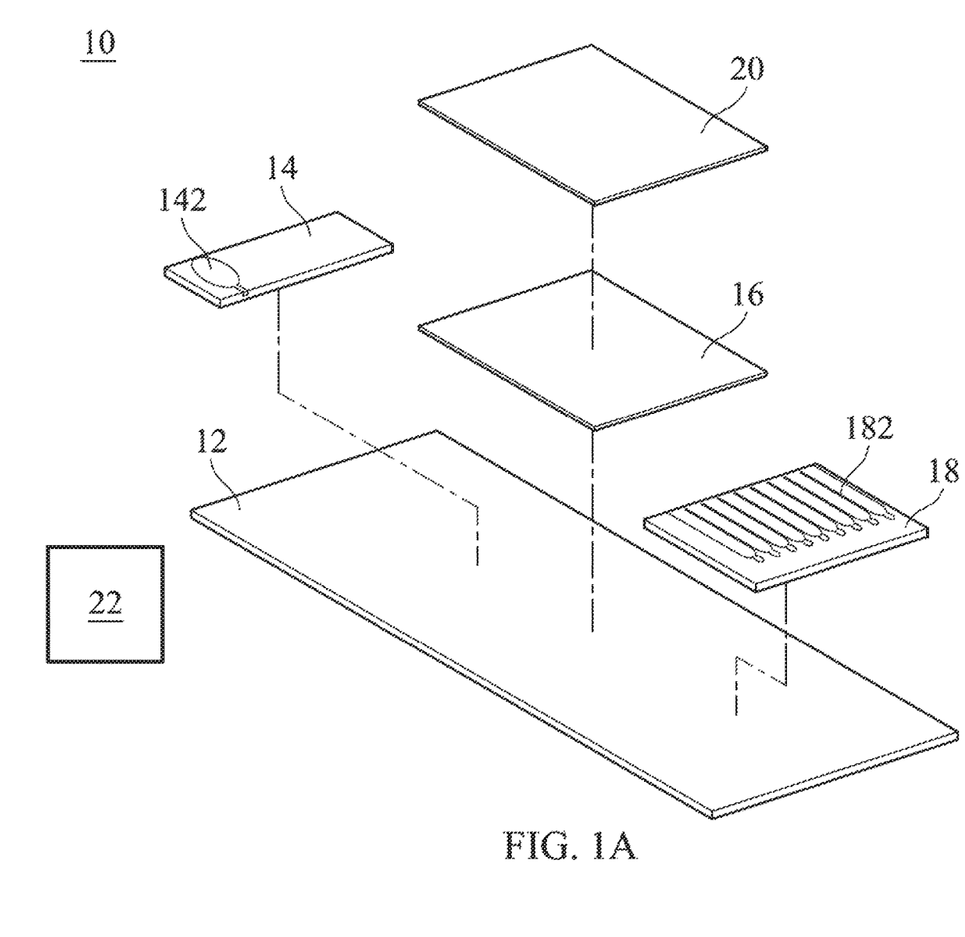
FIG. 1A shows an exploded view of the sorting device according to some embodiments of the present invention.
Figure 1B:
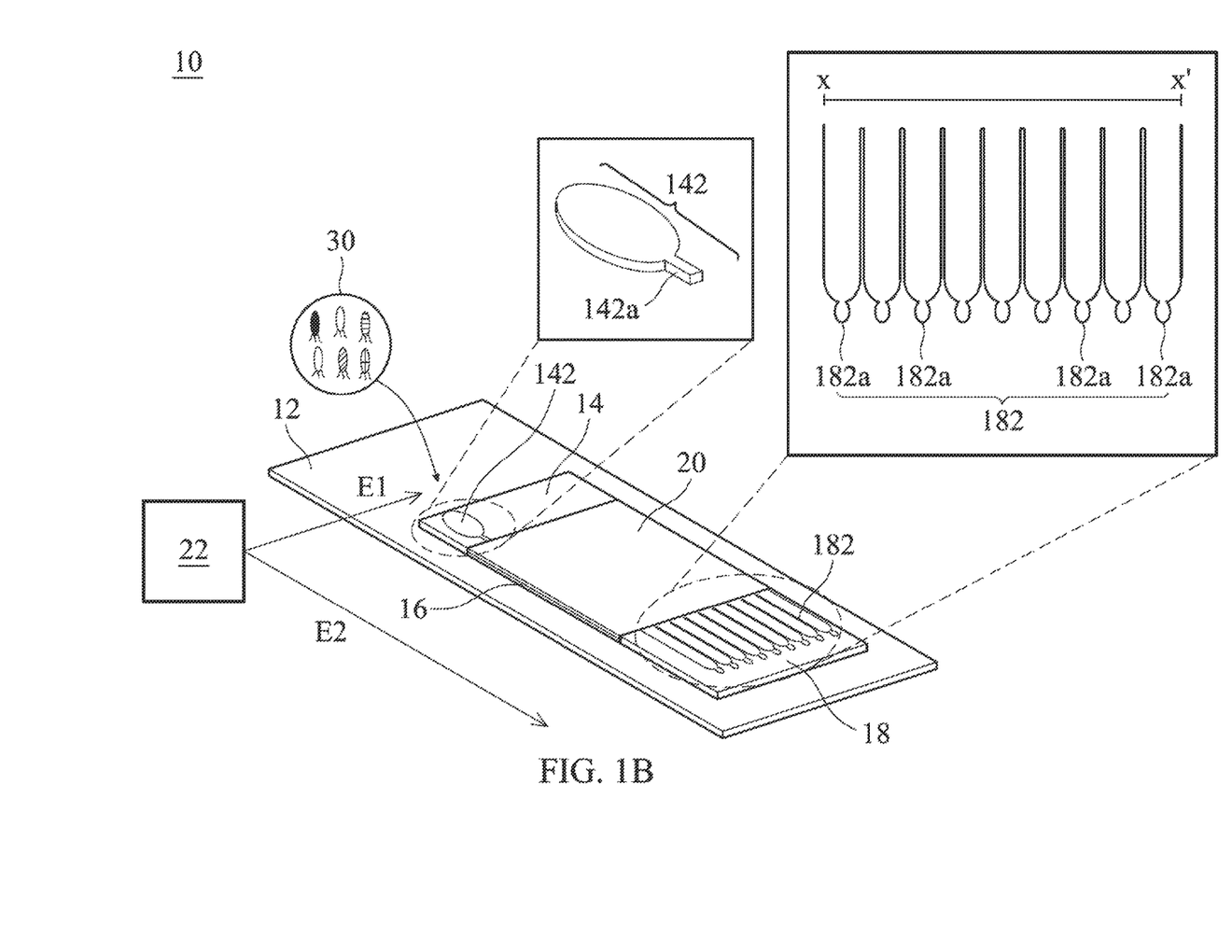
FIG. 1B shows a schematic diagram of the sorting device according to some embodiments of the present invention.

FIG. 1A and FIG. 1B respectively illustrate the exploded view and the schematic diagram of the sorting device according to some embodiments of the present invention. As shown in FIG. 1A and FIG. 1B, the sorting device 10 comprises: a carrier substrate 12, an input unit 14, a porous material 16, and an output unit 18.

The carrier substrate 12 may be made of a glass substrate, a silicon substrate, a plastic substrate, or combination thereof, but is not limited thereby. The input unit 14 is disposed on the carrier substrate 12 for inputting the biological sample 30 into the sorting device 10. In some embodiments, the biological sample 30 comprises the target biological analyte; and in the present embodiment, the biological sample 30 may be phage library or any solution that comprises target bacteriophage.

Furthermore, as illustrated in FIG. 1B, the input unit 14 may comprise an input hole 142, and the input hole 142 has an input channel 142a. In some embodiments, the length, the width, and the height of the input channel 142a may be 300 μm, 100 μm, and 100 μm, respectively. It should be noted that the size of the input hole 142 and the input channel 142a may be adjusted by a person skilled in the art according to the practical use in other embodiments.

The input unit 14 may be made of poly-dimethylsiloxane (PDMS), but is not limited thereby. In some embodiments, the input unit 142 may be formed by lithography, etching, photolithography or combination thereof.

Accordingly, the porous material 16 is disposed on the carrier substrate 12 and adjacent to the input unit 14. The porous material 16 contains an antigen having specificity to a target bacteriophage for sorting the bacteriophage. The porous material 16 may be made of agarose gel, polyacrylamide gel, filter paper, nitrocellulose, or combination thereof. In some embodiments, the porous material 16 may be made of 0.5 wt % to 20 wt % of agarose, for example, the porous material 16 may be made of 0.75 wt % of agarose.

Also, the concentration of the antigen added to the porous material 16 may be 1 μg/mL to 10 μg/mL or 4 μg/mL to 8 μg/mL. For example, the concentration of the antigen added to the porous material may be 8 μg/mL In some embodiments, the antigen may be fixed to the porous material 16 using a crosslinking agent. In some embodiments, two terminals of the crosslinking agent may be a peptide reactive terminal and a photo-reactive terminal, respectively. For example, the crosslinking agent may be sulfo-SANPAH, sulfo-SAND, sulfo-SFAD, sulfo-HSAB, sulfo-NHS-LC-ASA, sulfo-SASD, sulfo-SBED, sulfo-SAED, sulfo-SADP, or combination thereof.

Further, the output unit 18 is disposed on the carrier substrate 12 and adjacent to the porous material 16 for outputting the target bacteriophage sorted from the biological sample 30. The output unit 18 may be made of poly-dimethylsiloxane (PDMS), but is not limited thereby. The output unit 18 may be formed by lithography, etching, photolithography or combination thereof.

As shown in FIG. 1B, the output unit 18 further comprises a microfluidic channel unit 182. The microfluidic channel unit 182 comprises a plurality of channels 182a for collecting the sorted target bacteriophage. In some embodiments, the length, the width, and the height of the channel 182a of the microfluidic channel unit 182 may be 5 mm, 1.6 mm, and 0.1 mm, respectively. It should be noted that the size of the channel 182a of the microfluidic channel unit 182 may be adjusted by a person skilled in the art according to the practical use in other embodiments.

In some embodiments, the microfluidic channel unit 182 may be formed by casting from a patterned master mold. In some embodiments, the master mold is patterned by photolithography technique for forming a pre-designed microfluidic pattern drawn by computer graphics software in advance. In addition, the master mold of the microfluidic channel unit 182 may be made of the silicon wafer, glass, plastic, or combination thereof, but is not limited thereby.

In some embodiments, the aforementioned input unit 14 and the output unit 18 may be surface-modified by oxygen plasma process before attaching the input unit 14 and the output unit 18 to the carrier substrate 12.

Furthermore, as illustrated in FIG. 1A and FIG. 1B, the sorting device 10 may further comprise a cover plate 20 disposed on the porous material 16 for preventing the outer interferences against the antigen or biological sample in the porous material 16.

Moreover, the sorting device may further comprise a driving module for generating at least one driving force in the porous material 16 so as to sort the biological sample 30 based on the affinity for the antigen and the driving force. The driving force comprises a first driving force and a second driving force, wherein the direction of the first driving force differs from the direction of the second driving force, and the direction of the second driving force is toward the output unit 18. The intensity of the first driving force differs from the intensity of the second driving force, and the intensity of the second driving force is greater than the intensity of the first driving force. In the present embodiment, the driving module comprises an electric field generating unit 22 disposed on an external region of the carrier substrate 12 for generating a first electric field E1 and a second electric field E2 in the porous material 16, wherein the first electric field E1 provides the first driving force and the second electric field E1 provides the second driving force. In some embodiments, the electric field generating unit 22 may be an electrophoresis tank. In some embodiments, the direction of the first electric field E1 differs from the direction of the second electric field E2. In some embodiments, the direction of the first electric field E1 substantially perpendicular to the direction of the second electric field E2.

In some embodiments, the intensity of the first electric field E1 differs from the intensity of the second electric field E2. In some embodiments, the intensity of the first electric field E1 is smaller than the intensity of the second electric field E2. In some embodiments, the difference between the intensity of the first electric field and the intensity of the second electric field is 0.1 V/cm to 20 V/cm or 0.5 V/cm to 10 V/cm, for example, 2 V/cm.

It should be noted that in other embodiments, the intensity of the first electric field E1 and the second electric field E2 may be adjusted by a person skilled in the art based on the binding force between the target bacteriophage and the antigen for improving the sorting efficiency.

In addition, the first electric field E1 and the second electric field E2 may be alternatively generated in the porous material 16 by the electric field generating unit 22. In some embodiments, the alternating frequency of the first electric field E1 and the second electric field E2 may be 0.1 to 5 times per minute or 0.5 to 1.5 times per minute, for example, once per minute.

As shown in FIG. 1B, in some embodiments, the first electric field E1 and the second electric field E2, which are substantially perpendicular to each other and with different intensity (e.g. E1<E2), are generated alternatively in the porous material 16 by the electric field generating unit 22, so that the negative strains of bacteriophages unbound to or with weaker affinity for the antigen may be expelled out from the sorting device 10 along the direction of the first electric field E1 of weaker intensity. Also, the positive strain of bacteriophages (target bacteriophages) with greater affinity for the antigen may be transported to the microfluidic channel unit 182 along the direction of the second electric field E2.

It should be noted that positive strains of bacteriophages (target bacteriophages) mentioned above may be separated into different channels 182a of the microfluidic channel unit 182 along the direction of the first electric field E1 based on the affinity strength between the antigen and the target bacteriophage. For example, in the present embodiment, as shown in FIG. 1B, the affinity strength between positive strains of bacteriophages and the antigen weakens from x to x'.

Accordingly, the sorting device 10 may continuously and separately collect the target bacteriophage with different affinity for the antigen, and the amplification process and the confirmation process for the collected target bacteriophage need not to be performed, and the collected target bacteriophage may directly be applied.

It should be realized that the aforementioned case in which the first electric field E1 and the second electric field E2 are alternatively generated with directions substantially perpendicular to each other and with different intensity is only one embodiment of the present invention. As long as the first driving force and the second driving force with different intensities or directions may be achieved, the aforementioned case may be replaced thereby for implementing the present invention. For example, the first electric field E1 and the second electric field E2 may be generated continuously instead. Or a diagonal electric field may be generated either continuously or alternatively when the component forces in the directions same as the aforementioned first electric field E1 and second electric field E2 meet the requirement of the aforementioned embodiment. Also, a stream force may be the driving force of the driving module for replacing the aforementioned first electric field E1 or second electric field E2, or the stream force may be applied with the electric fields as long as the affinity of the target biological analyte and the antigen can be overcome.

Figure 2:
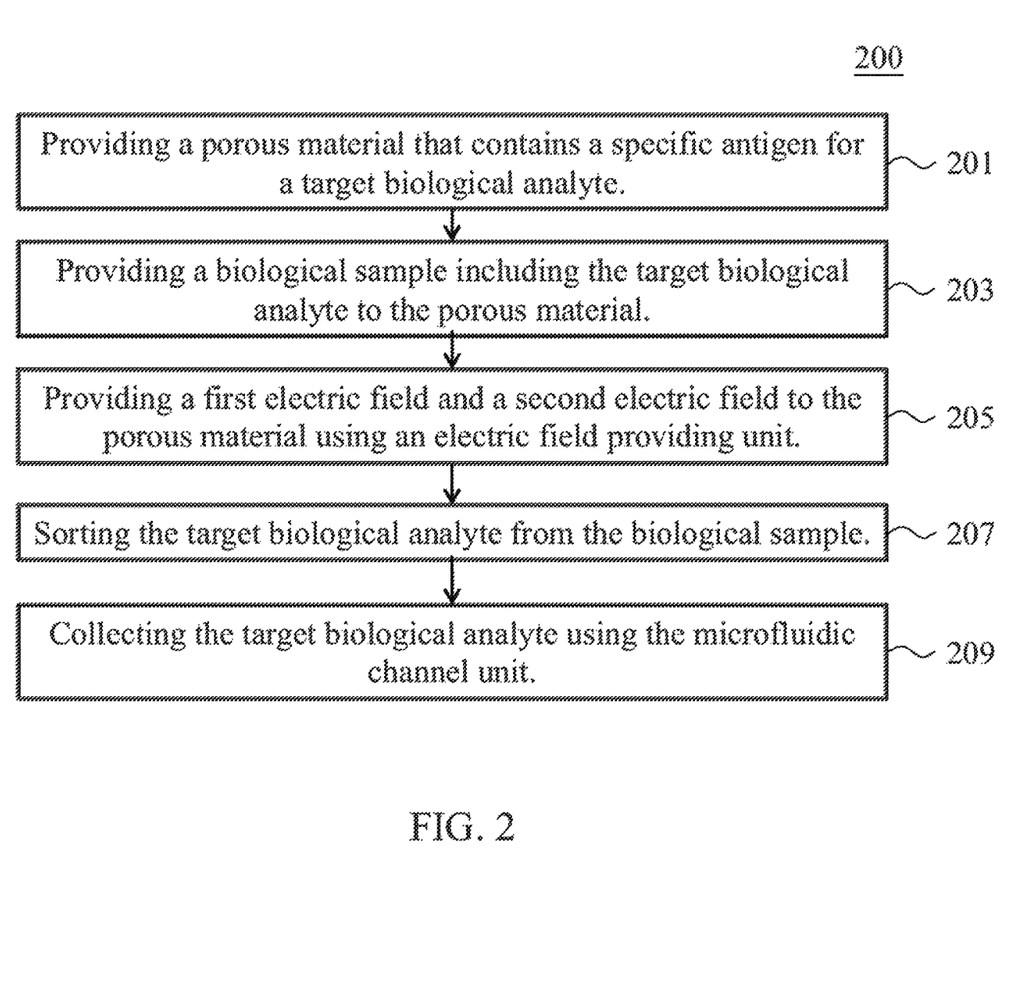
FIG. 2 shows a schematic diagram of the sorting method according to some embodiments of the present invention.

The following description will describe the sorting method using the sorting device 10 illustrated in FIG. 1A and FIG. 1B in embodiments. Similarly, the present embodiment may be applied for sorting biological analytes such as bacteriophages, antibodies, antigens, proteins, enzymes, metabolites, nucleic acids, drugs, and deoxyribonucleic acids (DNA). A sorting method for sorting target bacteriophage will be described as an example in the following description. FIG. 2 illustrates the flow chart of the sorting method 200 of some embodiments of the present invention.

Please refer to FIG. 1B and FIG. 2 simultaneously. First, a porous material 16 is provided in step 201, wherein the porous material 16 contains a specific antigen for a target biological analyte. A biological sample including the target biological analyte is introduced to the porous material 16 in step 203. In the present embodiment, the target biological analyte is bacteriophage; therefore, the biological sample 30 may be phage library or any solution that comprises the target bacteriophage. In some embodiments, the biological sample 30 may be input into the sorting device 10 by the input unit 14.

Hereafter, at least one driving force is generated in the porous material 16. In detail, a first electric field E1 and a second electric field E2 are generated in the porous material 16 by an electric field generating unit 22 in step 205.

The target bacteriophage in the biological sample 30 may be sorted in the porous material 16 by the antigen having specificity to the target bacteriophage, which is contained in the porous material 16. In detail, the target biological analyte may be sorted from the biological sample 30 contained in the porous material 16 based on its affinity for the antigen and the driving force in step 207. The porous material 16 may be made of agarose gel, polyacrylamide gel, filter paper, nitrocellulose, or combination thereof. In one embodiment, the porous material may be made of 0.5 wt % to 20 wt % of agarose, for example, 0.75 wt % of agarose.

Also, the concentration of the antigen added to the porous material 16 may be 1 μg/mL to 10 μg/mL, or 4 μg/mL to 8 μg/mL, for example, the concentration of the antigen added to the porous material may be 8 μg/mL In some embodiments, the antigen may be fixed to the porous material 16 using a crosslinking agent. In some embodiments, two terminals of the crosslinking agent may be peptide-reactive and photo-reactive, respectively. For example, the crosslinking agent may be sulfo-SANPAH, sulfo-SAND, sulfo-SFAD, sulfo-HSAB, sulfo-NHS-LC-ASA, sulfo-SASD, sulfo-SBED, sulfo-SAED, sulfo-SADP, or combination thereof.

Step 205 will be detailed described in the following description, wherein the first electric field E1 and the second electric field E2 with different directions are generated in the porous material 16 by the electric field generating unit for separating the bacteriophages. In some embodiments, the direction of the first electric field E1 and the direction of the second electric field E2 are substantially perpendicular to each other. In some embodiments, the intensity of the first electric field E1 differs from the intensity of the second electric field E2. In some embodiments, the intensity of the first electric field E1 is smaller than the intensity of the second electric field E2. In some embodiments, the difference between the intensity of the first electric field and the intensity of the second electric field is 0.1 V/cm to 20 V/cm or 0.5 V/cm to 10 V/cm, for example, 2 V/cm.

It should be noted that in other embodiments, the intensity of the first electric field E1 and the second electric field E2 may be adjusted by a person skilled in the art based on the affinity strength between the target bacteriophage and the antigen in order to improve the sorting efficiency.

Also, the first electric field E1 and the second electric field E2 may be generated alternatively in the porous material 16 by the electric field generating unit 22. In some embodiments, the alternating frequency of the first electric field E1 and the second electric field E2 may be 0.1 to 5 times per minute or 0.5 to 1.5 times per minute, for example, once per minute.

Next, the sorted target biological analyte (bacteriophage) may be collected in the microfluidic channel unit 182 in step 209. Please refer to FIG. 1B, in some embodiments, the first electric field E1 and the second electric field E2, which are substantially perpendicular to each other and with different intensity (e.g. E1<E2), are generated alternatively in the porous material 16 by the electric field generating unit 22, so that negative strains of bacteriophages unbound to or with weaker affinity for the antigen may be expelled out from the sorting device 10 along the direction of the first electric field E1 of weaker intensity. Also, positive strains of bacteriophages (target bacteriophage) with greater affinity for the antigen may be transported to the microfluidic channel unit 182 along the direction of the second electric field E2.

In the present embodiment, the target bacteriophage may be separated into different channels 182a of the microfluidic channel unit 182 along the direction of the first electric field E1 based on the affinity strength between the antigen and the target bacteriophage. For example, in the present embodiment, the affinity strength between the positive strains of bacteriophages and the antigen weakens from x to x' (please refer to FIG. 1B).

In some embodiment, the duration time of performing the sorting method 200 is approximately 40 minutes per cycle, that is, the duration time starting from inputting the biological sample 30 into the sorting device 10 till the target bacteriophage is collected in the microfluidic channel unit 182 is approximately 40 minutes per cycle. Comparing to the biopanning technique known in the art, which take 3 days for one cycle, the sorting method provided by the present invention is advantageous in saving time.

It should be realized that the aforementioned case in which the first electric field E1 and the second electric field E2 are alternatively generated with directions substantially perpendicular to each other and with different intensity is only one embodiment of the present invention. As long as the first driving force and the second driving force with different intensities or directions may be achieved, the aforementioned case may be replaced thereby for implementing the present invention. For example, the first electric field E1 and the second electric field E2 may be generated continuously instead. Or a diagonal electric field may be generated either continuously or alternatively when the component forces in the directions same as the aforementioned first electric field E1 and second electric field E2 meet the requirement of the aforementioned embodiment. Also, a stream force may be the driving force of the driving module for replacing the aforementioned first electric field E1 or second electric field E2, or the stream force may be applied with the electric fields as long as the affinity of the target biological analyte and the antigen can be overcome.

In summary, the target bacteriophage may be sorted rapidly and continuously with high throughput by the sorting device and the sorting method provided by the present invention. The target bacteriophage may then be further separated based on the affinity between the target bacteriophage and the antigen for improving the sorting accuracy.

Accordingly, the target bacteriophage sorted by the sorting device and method provided by the present invention may directly be applied without performing another subsequent test (such as ELISA). For example, the sorted target bacteriophage may directly be applied to manufacturing antibodies or vaccines, or may be applied as a target molecule in pharmaceutical development. In addition, the design of the microfluidic channel reduces the amount of the related reagents, and thus the cost of the sorting method may be reduced.

The following specific examples will be provided for implementing the technical features of the present invention.

However, these examples are illustrative, and the scope of the present invention should not be limited thereby.

EXAMPLE

[Soiling Device for Bacteriophage-Porous Material]

1% of agarose gel solution is prepared by mixing agarose gel powder and sterile water, then, 35 μL of sulfo-SANPAH (50 μg/mL) is added to and mixed with 100 μL of the 1% of agarose gel solution. The agarose gel solution is then disposed on the carrier substrate of the input unit and the output unit and covered by the cover plate. After the agarose gel solution is solidified, the solidified agarose gel is irradiated by 365 nm ultraviolet light for 3 minutes for activating the crosslink reaction of sulfo-SANPAH. One terminal of the sulfo-SANPAH may be fixed to the agarose gel, and another terminal of the sulfo-SANPAH may be fixed to proteins, thus antigens are capable of being fixed to the agarose gel. Next, the cover plate is removed to expose the agarose gel, and then 100 μL of antigen (8 μg/mL) is dropped onto the agarose gel. The antigen reacts with sulfo-SANPAH for forming a bonding structure to the agarose gel at 4° C. for 24 hours.

[Evaluation of the Sorting Result of the Sorting Device for Sorting Bacteriophage]

The positive strain of bacteriophages with a known sequence (fluorescent labeled) and the negative strain of bacteriophages are mixed in a ratio of 1:10 ($10^9:10^{10}$ C F U/mL), the bacteriophage mixture is then being sorted by the sorting device illustrated in FIG. 1B. The longitudinal electric field (5 V/cm) and the lateral electric field (3 V/cm) are generated alternatively (altering once per minute) to the sorting device by the electric generating device.

1. The amounts of the sorted positive strain of bacteriophages and the negative strain of bacteriophages are assessed by using the nanoparticle tracking analysis (NTA).

Figure 3A:
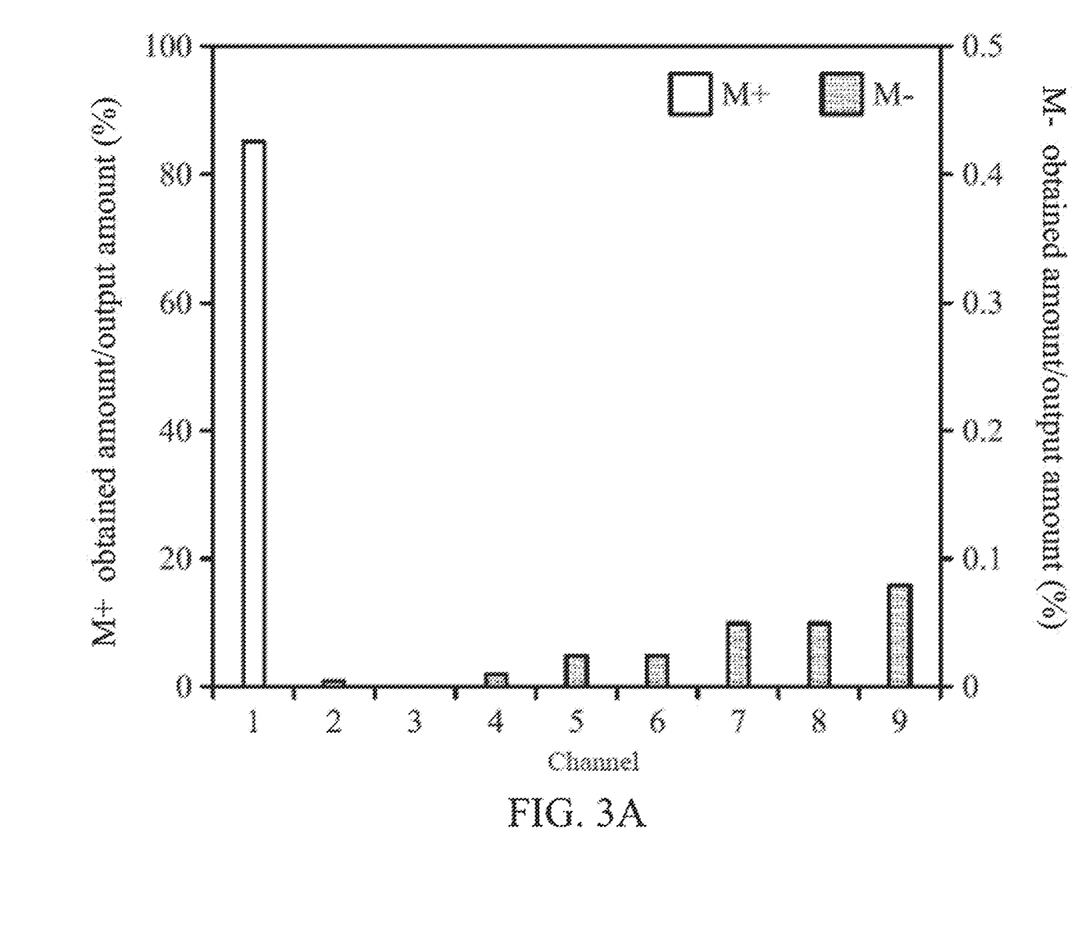
FIG. 3A and FIG. 3B show the number of the sorted target biological analyte evaluated by nanoparticle tracking analysis according to some embodiments of the present invention.
Figure 3B:
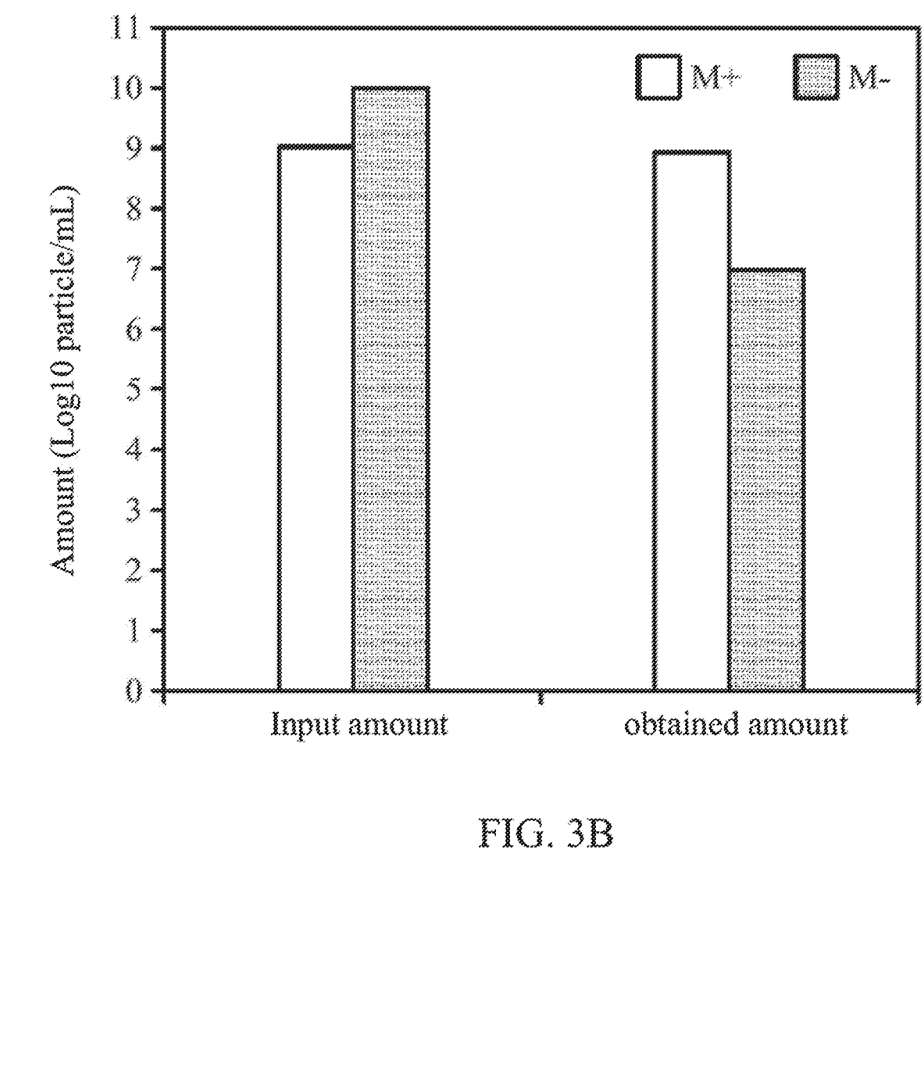

FIG. 3A and FIG. 3B show the result of nanoparticle tracking analysis for evaluating the amounts of the positive strain of bacteriophages and the negative strain of bacteriophages collected in each channel of the microfluidic channel unit, wherein M− represents the negative strain of bacteriophages and M+ represents the positive strain of bacteriophages in those figures, respectively. Refer to the result shown in FIG. 3A, the sorted positive strain of bacteriophages are concentrated in the channel 1 of the microfluidic channel unit (channel 1 corresponds to the channel closest to x in FIG. 1B; similarly, channel 9 corresponds to the channel closest to x' in FIG. 1B).

Further, the sorted positive strain of bacteriophages and the negative strain of bacteriophages are clearly separated. According to the result shown in FIG. 3A, the concentration of bacteriophages collected in channel 3 is below the detection limit of the NTA technique. In addition, as shown in FIG. 3B, the total recovery rate of the sorted positive strain of bacteriophages is above 85%.

2. The amounts of the sorted positive strain of bacteriophages and the negative strain of bacteriophages are evaluated by using enzyme-linked immunosorbent assay (ELISA).

Figure 4A:
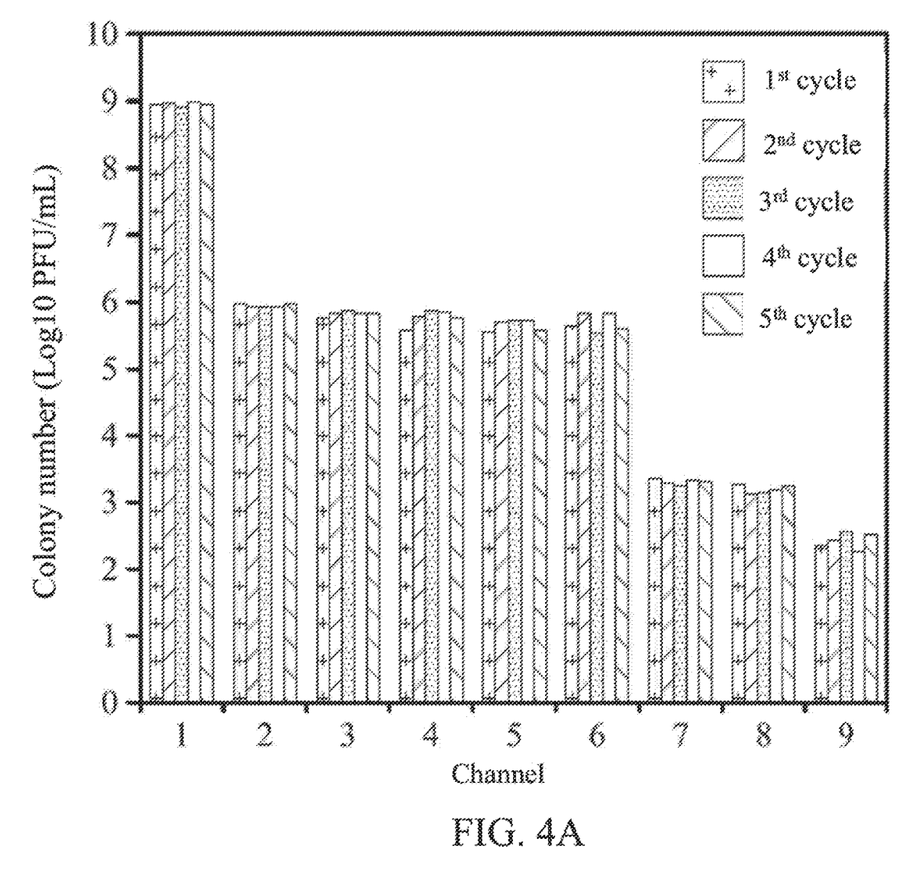
FIG. 4A and FIG. 4B show the number of the sorted target biological analyte evaluated by using enzyme-linked immunosorbent assay according to some embodiments of the present invention.
Figure 4B:
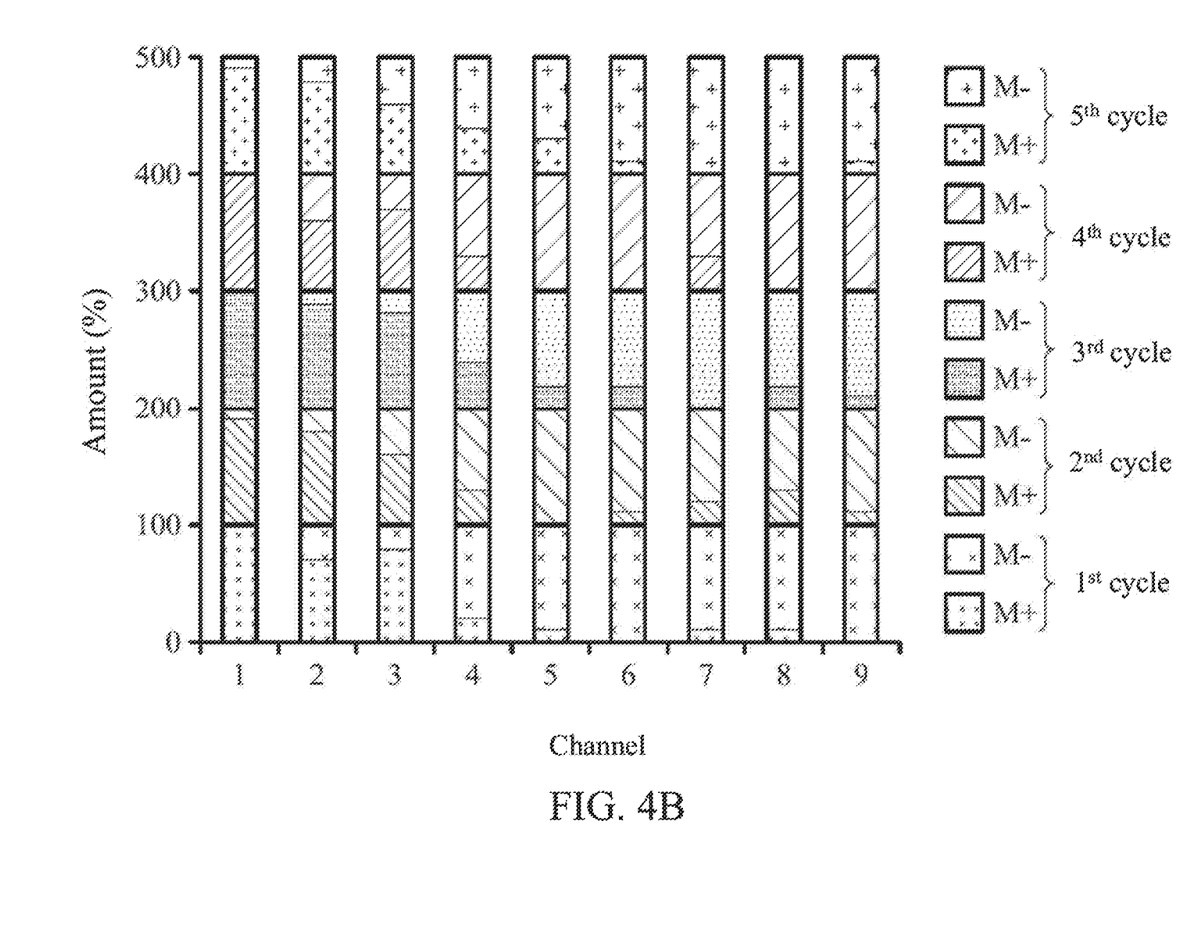

FIG. 4A and FIG. 4B show the result of enzyme-linked immunosorbent assay for evaluating the amount of the positive strain of bacteriophages and the negative strain of bacteriophages during the process of introducing the bacteriophage mixture continuously for 5 sorting cycles, wherein M− represents the negative strain of bacteriophages and M+ represents the positive strain of bacteriophages in those figures. According to the result shown in FIG. 4A and FIG. 4B, the sorting device is capable of performing the sorting process continuously and efficiently during the 5 sorting cycles tested. Therefore, the target bacteriophages may be sorted continuously with a high throughput by the sorting device of the present invention.

3. Detection of the DNA sequence of the sorted bacteriophage.

Table 1 shows the DNA sequencing results of the sorted bacteriophage. In detail, the DNA sequencing is performed by conducting the steps of infecting the E. coli with the sorted bacteriophage; plate-coating; and picking single colonies for sequencing. As shown in Table 1, 10 out of 10 single colonies infected with bacteriophages collected in channel 1 (corresponds to the channel closest to x in FIG. 1B) contain the sequence of the positive strain of bacteriophages. 8 out of 9 single colonies infected with bacteriophages collected in either channel 2, channel 3, or channel 6 contain the sequence of the positive strain of bacteriophages. Accordingly, the present invention has established a precise condition for sorting the positive strains of bacteriophages.

TABLE 1

| Channel No. | Number of the colonies sequenced | Number of the colonies with the sequence of the positive strain of bacteriophages (M+) | Number of the colonies with the sequence of the negative strain of bacteriophages (M−) | Ratio (M+/M−) | Percentage (%) |
|---|---|---|---|---|---|
| 1 | 10 | 10 | 0 | 10:0 | 100 |
| 2 | 9 | 8 | 1 | 8:1 | 88 |
| 3 | 9 | 8 | 1 | 8:1 | 88 |
| 6 | 9 | 8 | 1 | 8:1 | 88 |

In summary, the total recovery rate of the sorting device and sorting method is above 85%, wherein the proportion of the positive strain of bacteriophages is approximately 100%.

The aforementioned description illustrates the technical features of the embodiments so that many aspects of the present invention should be realized by those skilled in the art. It should be realized by those skilled in the art that advantages and effects of the embodiments may be easily achieved by other methods or structures designed or modified based on the features of the present invention, and it should also be realized these equivalent structures can be made without departing from the spirit and scope of the invention. Also, it is to be understood that many other possible modifications and variations can be made without departing from the spirit and scope of the invention as hereinafter claimed.

Although the present invention has been explained in relation to its aforementioned preferred embodiment, it is to be understood that many other possible modifications and variations can be made without departing from the spirit and scope of the invention as hereinafter claimed.

What is claimed is:

1. A sorting device, comprising:
  a carrier substrate;
  an input unit having an input hole and disposed on the carrier substrate for inputting a biological sample into the sorting device;
  a porous material disposed on the carrier substrate and adjacent to the input unit, wherein the porous material contains an antigen having specificity to a target biological analyte;
  a driving module generating at least one driving force in the porous material so as to sort the target biological analyte based on an affinity of the target biological analyte for the antigen and the driving force; and an output unit comprising a microfluidic channel unit disposed on the carrier substrate and adjacent to the porous material, the microfluidic channel unit comprising a pattern of microfluidic channels for collecting the target biological analyte sorted from the biological sample, wherein (i) the driving force comprises a first driving force and a second driving force, (ii) a direction of the first driving force is substantially perpendicular to a direction of the second driving force, and (iii) the porous material containing the antigen is configured to permit the target biological analyte and at least one nontarget analyte included in the biological sample to migrate different distances in the direction of the first driving force according to the difference in affinity between the target biological analyte and the antigen and between the nontarget analyte and the antigen and to move from the input unit toward the output unit along the direction of the second driving force.

2. The sorting device as claimed in claim 1, wherein the driving force is a stream force, an electric field force, or a combination thereof.

3. The sorting device as claimed in claim 1, wherein an intensity of the first driving force differs from an intensity of the second driving force, and the intensity of the second driving force is greater than the intensity of the first driving force.

4. The sorting device as claimed in claim 3, wherein the driving module comprises an electric field generating unit disposed on an external region of the carrier substrate for generating a first electric field and a second electric field in the porous material, wherein the first electric field provides the first driving force and the second electric field provides the second driving force.

5. The sorting device as claimed in claim 4, wherein the direction of the first electric field is substantially perpendicular to the direction of the second electric field.

6. The sorting device as claimed in claim 4, wherein a difference between an intensity of the first electric field and an intensity of the second electric field is 0.1 V/cm to 20 V/cm.

7. The sorting device as claimed in claim 4, wherein a difference between the intensity of the first electric field and the intensity of the second electric field is 0.5 V/cm to 10 V/cm.

8. The sorting device as claimed in claim 4, wherein the first electric field and the second electric field are alternatively generated in the porous material by the electric field generating unit.

9. The sorting device as claimed in claim 3, further comprising:

a cover plate disposed on the porous material.

10. The sorting device as claimed in claim 3, wherein the microfluidic channels are arranged at different locations in the direction of the first driving force, and the distance along the direction of the first driving force between the $N^{th}$ channel and the input hole is larger than that between the $(N-1)^{th}$ channel ($N \geq 2$) and the input hole.

11. The sorting device as claimed in claim 3, wherein the porous material includes agarose gel, polyacrylamide gel, filter paper, nitrocellulose, or combination thereof.

12. The sorting device as claimed in claim 1, wherein the target biological analyte is at least one selected from a group consisting of bacteriophages, antibodies, antigens, proteins, enzymes, metabolites, nucleic acids, drugs, and deoxyribonucleic acids (DNA).

13. The sorting device as claimed in claim 1, wherein the target biological analyte is bacteriophages.

\* \* \* \* \*